US00PP13050P2

(12) United States Plant Patent
Cadic

(10) Patent No.: US PP13,050 P2
(45) Date of Patent: Oct. 1, 2002

(54) FORSYTHIA PLANT NAMED 'COURDIJAU'

(75) Inventor: M. Alain Cadic, Beaucouze (FR)

(73) Assignee: Agri Obtentions S.A., Guyancourt Cedex (FR)

( * ) Notice: Subject to any disclaimer, the term of this patent is extended or adjusted under 35 U.S.C. 154(b) by 0 days.

(21) Appl. No.: 09/761,839

(22) Filed: Jan. 18, 2001

(51) Int. Cl.[7] ..... A01H 5/00
(52) U.S. Cl. ..... Plt./230
(58) Field of Search ..... Plt./230

(56) References Cited

PUBLICATIONS

UPOV–ROM GTITM Computer Database 2001/01, Feb. 6, 2001, GTI Jouve Retrieval Software, Citation for 'Courdijau'.*
Protection Des Obtentions Vegetales, Bulletin officiel du Comité de la Protection des Obtentions Végétales, No. 11 (1998), Cover Page and pp. 474 and 478.
Protection Des Obtentions Vegetales, Bulletin officiel du Comité de la Protection des Obtentions Végétales, No. 2 (1999), Cover Page and p. 48.

* cited by examiner

*Primary Examiner*—Bruce R. Campell
*Assistant Examiner*—Annette H. Para
(74) *Attorney, Agent, or Firm*—Burns, Doane, Swecker & Mathis, LLP

(57) ABSTRACT

A new and distinct cultivar of Forsythia plant is provided that is a seedling formed following the induced mutation of the 'Spring Glory' cultivar (non-patented in the United States). Gamma radiation was utilized to create the mutation. The new cultivar can be readily distinguished from the parent cultivar by the presence of a wide prostrate slow-growing growth habit. Anthocyanin coloration is present at the apex of the sepals. Attractive wide-opening yellow flowers are formed commonly on a single basis with one flower being formed per bud. The winter hardiness is good. The new cultivar also is well suited for growing as attractive ornamentation in the landscape where good control of plant height is to be maintained. The new cultivar requires no special care.

2 Drawing Sheets

BOTANICAL/COMMERCIAL CLASSIFICATION

*Forsythia×intermedia*/Forsythia.

VARIETAL DENOMINATION cv. 'Courdijau'.

SUMMARY OF THE INVENTION

A new and distinct cultivar of *Forsythia×intermedia* plant is provided that is a mutation derived from the 'Spring Glory' cultivar (non-patented in the United States).

When creating the new cultivar of the present invention plants of the 'Spring Glory' cultivar were irradiated with gamma rays, seeds were formed thereon following open pollination, and the seedlings produced upon the planting of such seeds were observed. The irradiation and the study of the resulting seedlings were carried out at the Institut National De La Recherche Agronomique located at Angers, France.

It was found that a single plant observed following such irradiation and the planting of seeds possessed the characteristics of the Forsythia cultivar of the present invention. The characteristics of such new cultivar can be summarized as follows:

(a) Exhibits a wide prostrate growth habit,
(b) Bears anthocyanin coloration at the apex of the sepals,
(c) Forms attractive dense wide-opening yellow flowers that commonly are borne singly per bud, and
(d) Is slow-growing and requires no special care.

The new cultivar of the present invention well meets the needs of the horticultural industry and is particularly well suited for growing as attractive ornamentation in the landscape. The yellow blossoms are densely formed in the springtime. Such dense flowering is manifest even though only one flower commonly is produced per flowering bud.

The new cultivar of the present invention can be readily distinguished from plants of the 'Courtasol' cultivar (U.S. Plant Pat. No. 9,104) and the 'Courtacour' (U.S. Plant Pat. Application Ser. No. 09/607,278, filed Jun. 30, 2000) that also were derived from the 'Spring Glory' cultivar (non-patented in the United States). More specifically, the new cultivar is very slow growing and assumes a more prostrate configuration than the 'Courtacour' variety. Also, the flowers commonly are borne singly and not in clusters as the 'Courtasol' cultivar.

The new cultivar grows well in containers, tubs and pots and can be grown on balconies and terraces. It can be grown to advantage wherever an attractive wide and low-growing ornamental plant is desired.

The new cultivar has been found to readily undergo asexual propagation by the use of softwood cuttings. Roots readily form on such cuttings during the summer. Such asexual propagation has been carried out at Angers, France, and elsewhere, and has confirmed that the new cultivar reproduces true to type.

The new cultivar has been named the 'Courdijau' cultivar.

BRIEF DESCRIPTION OF THE PHOTOGRAPH

The accompanying photographs show plants and plant parts when blossoming in the springtime at Angers, France.

FIG. 1 depits on Apr. 5, 1997 a twelve year-old plant of the new cultivar having a prostrate growth habit. The plant was approximately 90 cm in height and approximately 120 cm in width.

DETAILED DESCRIPTION

Figure 1:
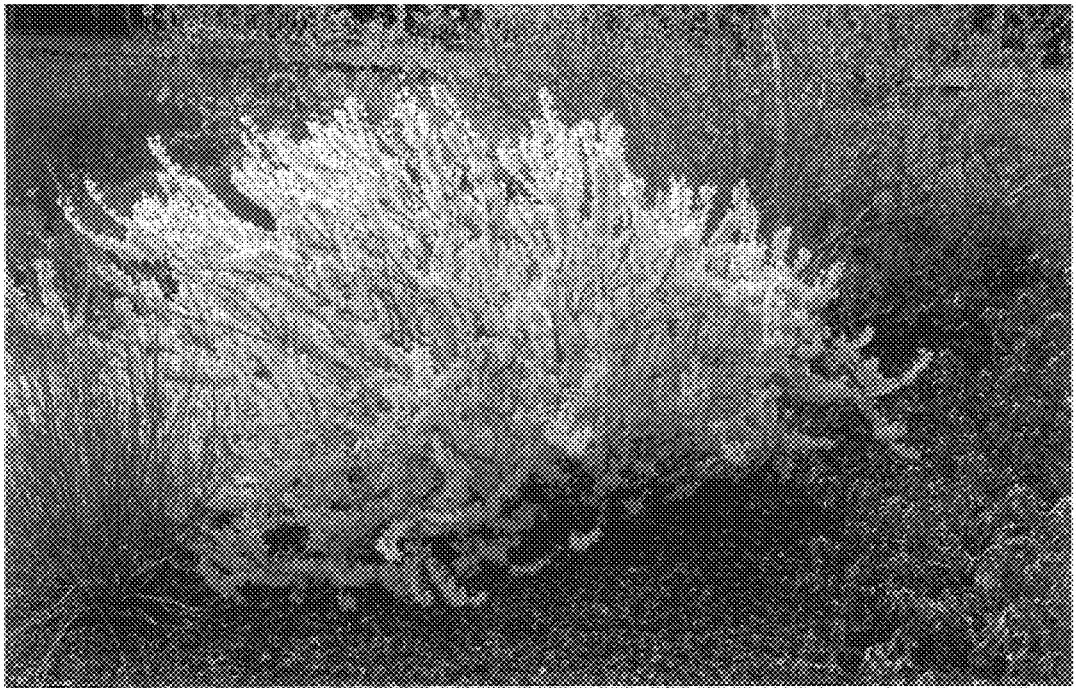
Figure 2:
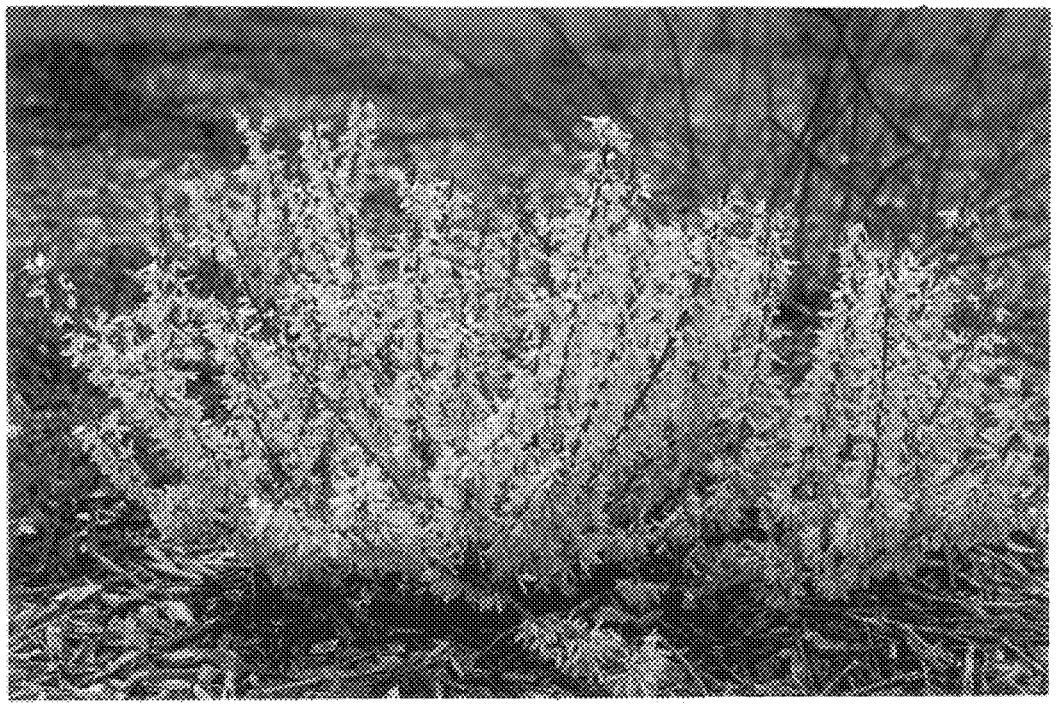
FIG. 2 depicts on Mar. 3, 1990 a five year-old plant of the new cultivar.
Figure 3:
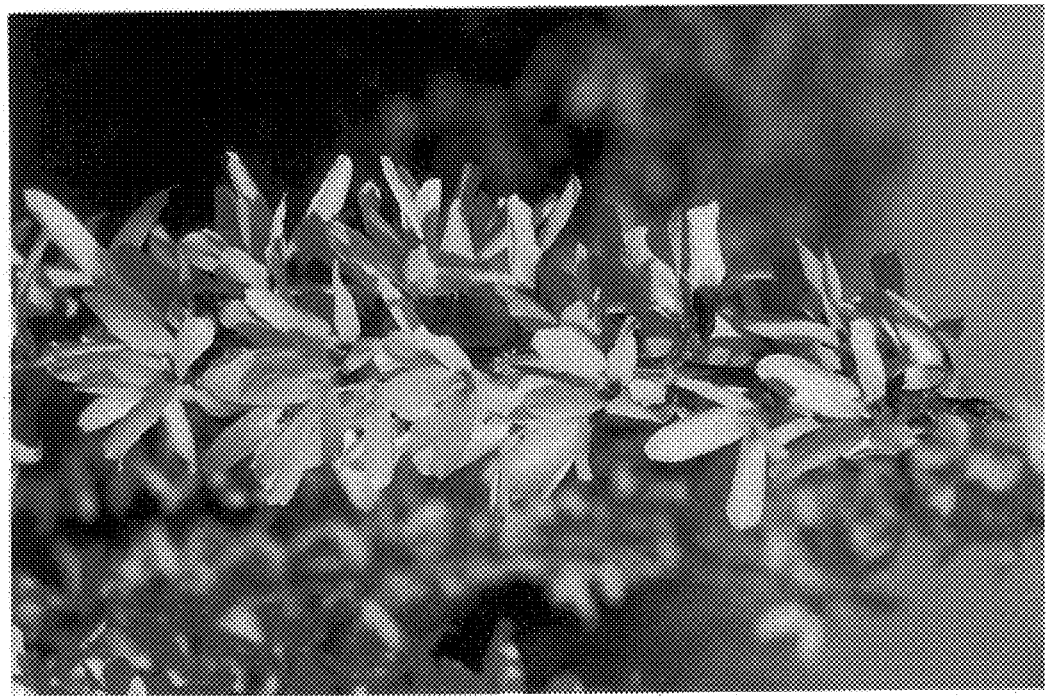
FIG. 3 depicts on Mar. 1, 1990 a flowering shoot of the new cultivar. The attractive flowering is dense even though only one flower is produced per flowering bud.
Figure 4:
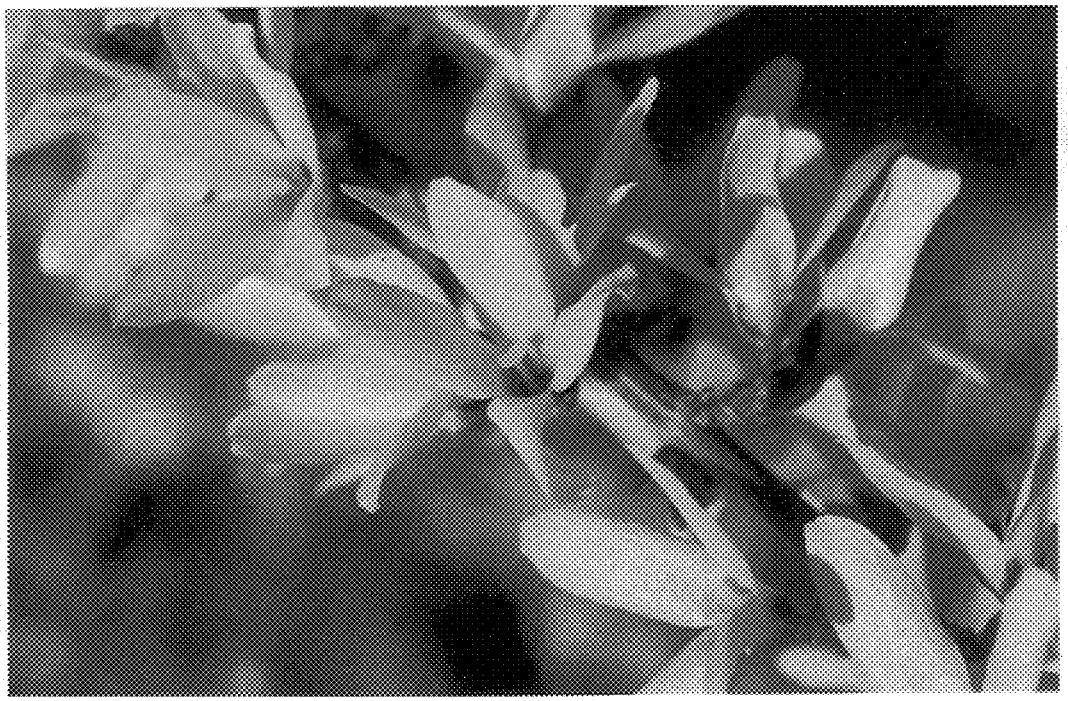
FIG. 4 depicts on Mar. 10, 1990 a close view of a typical flower of the new cultivar. The petal shape, style, and anthocyanin coloration at the apex of the sepals are apparent.

The following description is based on the observation of mature plants of the new cultivar growing outdoors at Angers, France. Such plants have been asexually reproduced through the use of softwood cuttings. The color terminology utilized in the description that follows is to be accorded its ordinary dictionary significance. Reference to The R.H.S. Colour Chart of The Royal Horticultural Society, London, England, sometimes is included.

Origin: Seedling produced following the induced mutation of the 'Spring Glory' cultivar (non-patented in the United States). The 'Spring Glory' cultivar was irradiated with gamma rays from cobalt 60.

Parentage: Seedling of 'Spring Glory'.

Classification: *Forsythia×intermetia,* cv. 'Courdijau'.

Plant:

*Form.*—Well-branched slow-growing flowering shrub.

*Habit.*—Prostrate, and spreading. The plant is considered to be a wide and very low-growing dwarf unlike its 'Spring Glory' parent.

*Internode length.*—Exceptionally short, considerably shorter than that of the parent 'Spring Glory' cultivar. Typical internode lengths are approximately 10 mm or less on one year-old shoots of approximately 10 to 20 cm in length.

*Shoot pith.*—Lamellate throughout the length.

*Height.*—At an age of 12 years a height of approximately 90 cm, and at an age 16 years a height of approximately 1 m on a plant that had been lightly pruned two times.

*Width.*—At the age of 12 years a width of approximately 1.2 m, and at the age of 16 years a width of approximately 1.5 m on a plant that had been lightly pruned two times.

Foliage:

*Disposition.*—Opposite, and commonly begins to appear during flowering.

*Configuration.*—Ovate and simple.

*Color.*—Yellow-Green Group 146B on the upper surface and Yellow-Green Group 146D on the under surface.

Inflorescence:

*Configuration.*—Wide-opening.

*Size.*—Medium.

*Calyx tube.*—Approximately 1.4 mm in length on average.

*Color.*—Yellow Group 12B.

*Peduncle.*—Approximately 5.9 mm in length on average.

*Sepals.*—Green in coloration, ciliated, bear anthocyanin coloration at the apex of the sepals, approximately 3.8 mm in length on average and approximately 2.4 mm in width on average.

*Petals.*—Approximately 6.1 mm in width on average.

*Disposition.*—Flowers are densely borne and commonly are borne singly with one flower per bud.

*Anthers.*—Disposed below the stigma. The distance between the stigma and the top of the anthers commonly is approximately 2.7 mm. The coloration is pale greenish-yellow to whitish before anthesis. The anther length is approximately 2 mm.

*Filaments.*—Approximately 1.5 mm in length on average. The coloration is pale greenish-yellow to whitish.

*Stamens.*—Approximately 3.5 mm in length on average and significantly smaller than the styles. The small size precludes an characterization the coloration.

*Pistil.*—Approximately 6.6 mm in length on average and greenish in coloration.

*Styles.*—Long, Yellow Group 3B in coloration, and end in a bilobed stigma. In a fully-opened flower the stigma protrudes clearly from the corolla tube.

*Time of flowering.*—Springtime.

*Petal drop.*—Medium tendency to detach.

*Fruits and seeds.*—None observed during observation to date.

Growing conditions: Does well in full sun or semi-shade, and prefers soil that is not exceedingly dry.

Hardiness: Very good. Has withstood temperatures of −25° C. to −30° C.

Disease resistance: Like other Forsythia cultivars the new cultivar is not commonly prone to disease.

Insect resistance: Like other Forsythia cultivars the new cultivar commonly displays no noticeable insect damage.

Drought resistance: Believed to be comparable to that of other commonly grown Forsythia cultivars.

Propagation: Can be readily propagated while utilizing softwood cuttings.

Usage: Attractive wide and low-growing ornamental spring-flowering shrub for growing in pots, tubs or containers in small gardens, balconies and terraces. Alternatively can be grown in the landscape. Requires no special care.

I claim:

1. A new and distinct Forsythia plant that is derived from the 'Spring Glory' cultivar (non-patented in the United States) having the following combination of characteristics:

(a) Exhibits wide prostrate growth habit, (b) Bears anthocyanin coloration at the apex of the sepals, (c) Forms attractive dense wide-opening yellow flowers that commonly are singly borne per bud, and (d) Is slow-growing and requires no special care;

substantially as shown and described.

* * * * *